US 9,631,955 B2

(12) United States Patent
Campbell et al.

(10) Patent No.: US 9,631,955 B2
(45) Date of Patent: Apr. 25, 2017

(54) METHOD OF ASSEMBLING A SUBSEA SENSOR

(71) Applicant: General Electric Company, Schenectady, NY (US)

(72) Inventors: Lam Arthur Campbell, Tomball, TX (US); Dan Tho Lu, Minden, NV (US); Svein Arild Haugen, Bergen (NO); Jens Abrahamsen, Bergen (NO)

(73) Assignee: General Electric Company, Schenectady, NY (US)

( * ) Notice: Subject to any disclaimer, the term of this patent is extended or adjusted under 35 U.S.C. 154(b) by 313 days.

(21) Appl. No.: 14/258,509

(22) Filed: Apr. 22, 2014

(65) Prior Publication Data

US 2015/0300848 A1   Oct. 22, 2015

(51) Int. Cl.
*G01D 11/24* (2006.01)
*G01D 5/20* (2006.01)
(Continued)

(52) U.S. Cl.
CPC ........ *G01D 11/245* (2013.01); *E21B 33/0385* (2013.01); *E21B 47/0905* (2013.01);
(Continued)

(58) Field of Classification Search
CPC ...... E21B 4/02; E21B 41/0085; E21B 43/121; E21B 47/01; E21B 33/0385;
(Continued)

(56) References Cited

U.S. PATENT DOCUMENTS

| 5,166,677 A | 11/1992 | Schoenberg |
| 5,219,068 A | 6/1993 | Piotrowski |

(Continued)

FOREIGN PATENT DOCUMENTS

CN        201241695 Y      5/2009

OTHER PUBLICATIONS

PCT Search Report and Written Opinion issued in connection with corresponding PCT Application No. PCT/US2015/024802 on Jun. 29, 2015.

(Continued)

*Primary Examiner* — Carl Arbes
(74) *Attorney, Agent, or Firm* — Armstrong Teasdale LLP

(57) ABSTRACT

Sensor assemblies and methods of assembling and using the sensor assemblies are provided for monitoring operational characteristics of subsea rotating devices such as subsea motors and pumps. Pressure-compensated proximity sensor tip assemblies configured to withstand subsea pressures are mounted adjacent a subsea rotating shaft for directly monitoring a position of the rotating shaft during dynamic operation thereof. An end of a sensor housing opposite a sensor tip assembly is mounted to a wall of the device housing. The sensor housing defines a fluid reservoir containing a substantially incompressible fluid therein that is in fluid communication with the interior portions of the proximity sensor tip assembly. A length of the sensor housing is adjusted to accommodate a distance between the wall of the device housing and the rotating shaft.

17 Claims, 5 Drawing Sheets

(51) Int. Cl.
  *G01D 11/30* (2006.01)
  *E21B 33/038* (2006.01)
  *E21B 47/09* (2012.01)
  *G01N 27/72* (2006.01)
(52) U.S. Cl.
  CPC ........... *G01D 5/2013* (2013.01); *G01D 11/30* (2013.01); *G01N 27/72* (2013.01)
(58) Field of Classification Search
  CPC ............. G01L 5/0076; Y10T 29/49242; Y10T 29/49771; Y10T 29/49826; G01D 5/2013; G01D 11/245; G01D 11/30; G01N 27/72
  See application file for complete search history.

(56) References Cited

U.S. PATENT DOCUMENTS

| | | | |
|---|---|---|---|
| 2009/0169364 A1* | 7/2009 | Downton | B22D 15/00 415/118 |
| 2010/0065336 A1 | 3/2010 | Wells et al. | |
| 2010/0299119 A1 | 11/2010 | Erikson | |
| 2012/0098674 A1 | 4/2012 | McStay | |
| 2012/0279720 A1* | 11/2012 | Whitby | E21B 33/0355 166/363 |
| 2013/0192859 A1 | 8/2013 | Holiday et al. | |
| 2013/0272898 A1 | 10/2013 | Toh | |
| 2014/0035604 A1 | 2/2014 | Rongve | |

OTHER PUBLICATIONS

PCT Search Report and Written Opinion issued in connection with PCT Application No. PCT/US2015/024663 on Jun. 23, 2015. That application corresponds to related U.S. Appl. No. 14/258,735.

Bently Nevada Applications Note, Standardized Rules for Measurement on Rotating Machinery, pp. 1-5.

Applications Note, Vibration Measurement—Basic Parameters for Predictive Maintenance on Rotating Machinery, pp. 1-5.

* cited by examiner

METHOD OF ASSEMBLING A SUBSEA SENSOR

RELATED APPLICATIONS

This application contains subject matter related to copending patent applications including U.S. patent application Ser. No. 14/258,735 filed herewith, entitled "Subsea Sensor Assemblies," and U.S. patent application Ser. No. 14/258,880 filed herewith, entitled "Subsea Sensor Assemblies," each of which is incorporated by reference herein in its entirety.

BACKGROUND OF THE INVENTION

1. Field of the Invention

This present invention relates to sensor assemblies operable in harsh environments such as high-pressure subsea applications. In particular, the invention relates to proximity sensor probes operable to monitor the performance of rotating equipment such as subsea pumps and motor assemblies installed in an underwater fluid extraction well.

2. Description of the Related Art

In many subsea fluid extraction wells, equipment such as rotary motors are positioned at the sea floor or at a downhole location to control the production and delivery of hydrocarbons to the sea surface. Much of this equipment is subject to wear, and therefore needs to be repaired or replaced periodically. Since the condition in which this equipment operates varies greatly from application to application, and since every situation is unique, proper maintenance intervals can be difficult to predict. When proper maintenance intervals are underestimated, equipment failure and an associated emergency halt in production often results.

To help assess the need for maintenance, various sensor assemblies have been provided to monitor indirect parameters related to equipment health such as temperature, pressure and flow rates. In one example application, accelerometers mounted to a motor case indirectly monitor a motor shaft by monitoring movement of the motor case that may have been caused by an unbalance or vibration of the motor shaft. Often, this method is not very accurate. At least since the environmental conditions encountered in subsea fluid extraction wells are generally unique for each application, a problematic accelerometer data pattern may not be immediately recognized. Also, since the motor case is generally much heavier than motor shaft, small variations in the movement of the motor shaft induce even smaller variations in the movement of the motor case. Thus, in some instances, problematic movements of the motor shaft are not recognized in the early stages and persist until the movements become more pronounced. This delay can be associated with poor diagnostic information.

One application in which indirect monitoring can provide poor diagnostic information is in a subsea booster pump that employs fluid film bearings. Fluid film bearings generally support their loads on a thin layer of liquid or gas, and are frequently used in high load or high speed applications where ball bearings would wear quickly or cause excessive noise or vibration. In some instances, fluid film bearings permit a motor shaft to rotate in an off-center or elliptical orbit when properly operating, and these orbits can be difficult to distinguish from problematic rotational patterns using indirect methods such as detecting a problematic acoustic signature.

Accordingly, recognized is the need for directly monitoring a motor shall for assessing the health of the motor used in subsea applications. Direct monitoring of a motor shaft can include monitoring dynamic motion parameters such as vibrational amplitude, frequency and phase angle, as well as static, quasi-static or steady state position measurements such as steady state eccentricity position, axial thrust position and eccentricity slow roll. Other parameters of a motor shaft can be directly monitored to facilitate assessing motor health. Also recognized is the need for providing such a sensor assembly that can be readily installed into existing motor assemblies to directly monitor the motor shaft in a variety of configurations and orientations.

SUMMARY OF THE INVENTION

In view of the foregoing, various embodiments of the present invention advantageously provide sensor assemblies for monitoring operational characteristics of subsea pumps, motors and other rotating devices. Various aspects of the present invention advantageously provide proximity sensor assemblies that are operable to directly detect the position of a rotating shaft without physical contact with the shaft. Proximity sensors typically actively emit RF (radio-frequency) radiation, light, sound, or other types of energy, and detect changes in the electromagnetic field or return signal. Proximity sensor assemblies in accordance with embodiments of the present invention are configured to withstand pressures of 1035 bar or more, as well as other subsea environmental conditions. Embodiments of the present invention are sufficiently flexible and adjustable to provide an EC (eddy current) sensor cap or similar proximity sensor tip adjacent a motor shaft in a variety of motor configurations. Various aspects of the present invention permit monitoring of subsea or other harsh environment equipment in accordance with standards API 670 and API 610, which generally apply to industrial topside machinery.

According to one aspect of the invention, a method of assembling and using pressure-compensated proximity sensors for monitoring the condition of a subsea rotating device includes the steps of: (1) mounting a pressure-compensated proximity sensor tip assembly within a device housing of the subsea rotating device, to include disposing a sensing element within interior portions of the proximity sensor tip assembly, the sensing element configured to detect a rotating shaft of the subsea rotating device and produce a signal indicative of a distance between a reference point on the proximity sensor tip assembly and a portion of the rotating shaft; (2) mounting an end of a sensor housing connected to the proximity sensor tip assembly to a wall of the device housing, the sensor housing defining a fluid reservoir containing a substantially incompressible fluid therein that is in fluid communication with the interior portions of the proximity sensor tip assembly; and (3) adjusting a length of the sensor housing to accommodate a distance between the wall of the device housing and the rotating shaft.

According to another aspect of the present invention, a method of assembling and monitoring the condition of a subsea rotating device including a device housing and a rotating shaft disposed at least partially within the device housing includes the steps of: (1) providing a pressure-compensated proximity sensor tip assembly within the device housing, the proximity sensor tip assembly having a sensing element disposed within interior portions of the proximity sensor tip assembly, the sensing element configured to detect the rotating shaft and produce a signal indicative of a distance between a reference point on the proximity sensor tip assembly and a reference point on the rotating shaft; (2) submerging the subsea rotating device into a subsea environment such that an environmental pressure is applied to an exterior of the sensor tip assembly; (3) transmitting a portion of the environmental pressure to interior portions of the sensor tip assembly; (4) dynamically operating the subsea rotating device in the subsea environment such that the rotating shaft rotates within the device housing; and (5) detecting, with the pressure-compensated proximity sensor tip assembly, a displacement of the rotating shaft between a static configuration wherein the rotating shaft is stationary with respect to device housing and a dynamic configuration wherein the rotating shaft rotates within device housing.

According to another aspect of the present invention, a method of assembling and using pressure-compensated proximity sensors for monitoring the condition of a subsea rotating device includes the steps of: (1) mounting a pressure-compensated proximity sensor tip assembly within a device housing of the subsea rotating device, to include disposing a sensing element within interior portions of the proximity sensor tip assembly, the sensing element configured to detect a rotating shaft of the subsea rotating device and produce a signal indicative of a distance between a reference point on the proximity sensor tip assembly and a portion of the rotating shaft; (2) mounting an end of a sensor housing connected to the proximity sensor tip assembly to a wall of the device housing, the sensor housing defining a fluid reservoir containing a substantially incompressible fluid therein that is in fluid communication with the interior portions of the proximity sensor tip assembly; (3) adjusting a length of the sensor housing to accommodate a distance between the wall of the device housing and the rotating shaft; (4) submerging the subsea rotating device into a subsea environment such that an environmental pressure is applied to an exterior of the proximity sensor tip assembly; (5) transmitting a portion of the environmental pressure to interior portions of the proximity sensor tip assembly; (6) dynamically operating the subsea rotating device in the subsea environment such that the rotating shaft rotates within the device housing; and (7) detecting, with the proximity sensor tip assembly, a displacement of the rotating shaft between a static configuration wherein the rotating shaft is stationary with respect to device housing and a dynamic configuration wherein the rotating shaft rotates within device housing.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

DETAILED DESCRIPTION

The present invention will now be described more fully hereinafter with reference to the accompanying drawings, which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout. Prime notation, if used, indicates similar elements in alternative embodiments.

Figure 1:
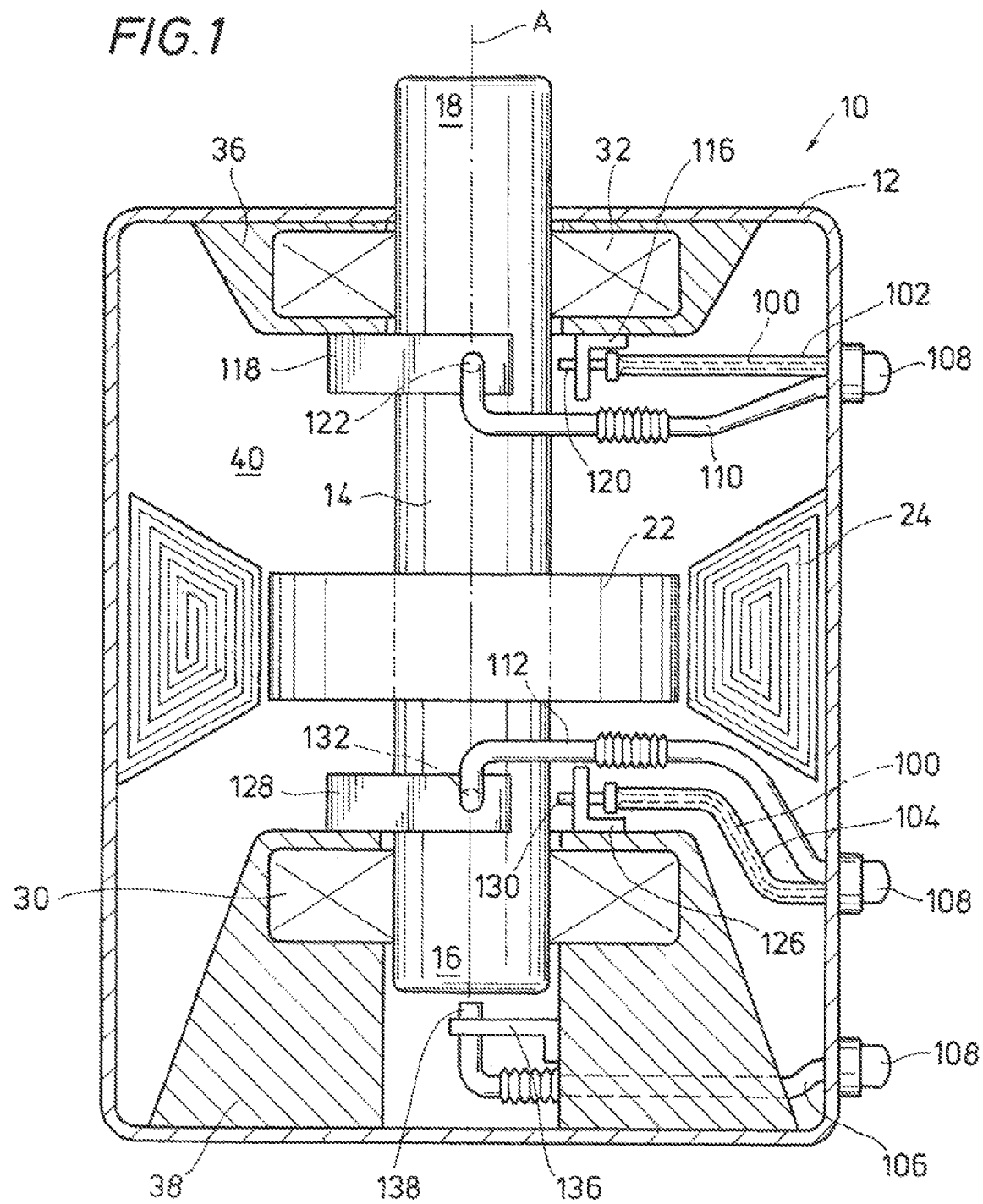
FIG. 1 is an environmental view of a subsea motor assembly with a plurality of penetrator assemblies extending through a motor housing of the motor assembly, according to an example embodiment of the present invention.

Referring to FIG. 1, subsea motor assembly 10 is an example subsea device, which illustrates example aspects of the present invention. As illustrated in FIG. 1, adjustable-length sensor assemblies are integrated within the penetrator assemblies and installed within subsea motor assembly 10. Adjustable length sensor assemblies are installed in other locations within the motor housing for directly monitoring a position of a motor shaft Subsea motor assembly 10 includes a motor case or other type of motor housing 12. Motor shaft 14 is disposed at least partially within motor housing 12 such that motor shaft 14 has an interior end 16 disposed within motor housing 12 and an exterior end 18 extending to an exterior of motor housing 12. Exterior end 18 is operable to be coupled to a pump, drilling motor, tractor, vibrator or other component (not shown) to be driven by the motor. In some embodiments, exterior end 18 is coupled to a shaft 176 (see FIG. 2) of a booster pump 150 for providing artificial lift to facilitate extraction of fluids from a well. Rotor 22 and stator 24 drive motor shaft 14 as is understood in the art.

Motor shaft 14 is supported by lower bearing assembly 30 and upper bearing assembly 32 along a longitudinal axis "A"

when in a static state such that motor shaft 14 is stationary with respect to motor housing 12. Upper and lower bearing assemblies 30, 32 include both thrust and radial bearings for supporting axial and radial loads. In some embodiments, at least some of the thrust and radial bearings are fluid film bearings, which support their loads on a thin layer of liquid or gas as indicated above. As understood by those skilled in the art, in some embodiments, motor shaft 14 rotates in a generally elliptical orbit about axis "A" when supported by fluid-film bearings. The extent or degree of the elliptical orbit can be dependent on a degree of wear of the fluid-film bearings. As recognized by those skilled in the art, other types of bearing assemblies are susceptible to non-circular orbits such as tilt-pad bearings or active magnetic bearings. Bearing assemblies 30, 32 are supported within motor housing 12 by respective base supports 36, 38. In some embodiments, base supports 36, 38 are formed integrally with motor housing 12, and in some embodiments base supports have a relatively large mass with respect to motor shaft 14.

To monitor a position of motor shaft 14, a plurality of proximity sensor probe assemblies 100, 110, 112 are provided. Some of the proximity sensor assemblies 100 can be integrated into integrated penetrator and proximity sensor probe assemblies 102, 104 and 106, which penetrate motor housing 12 such that a portion of each integrated penetrator and proximity sensor probe assembly 102, 104, 106 is disposed on an interior of the motor housing 12 proximate motor shaft 14, and a portion of each penetrator assembly is disposed on an exterior of motor housing 12. As one skilled in the art will appreciate, a penetrator assembly generally facilitates passage of cables and other wiring through a bulkhead or instrument package, and in some instances, with fewer seals than a standard connector set. The portions of the integrated penetrator and proximity sensor probe assembly 102, 104, 106 disposed on an exterior of motor housing 12 include respective electronics packages 108. Electronic packages 108 enable communication of electrical power, signal conditioning, information and/or other media between the integrated penetrator and proximity sensor probe assemblies 102, 104, 106 and other subsea, down-hole or surface equipment, or other equipment exterior to motor housing 12, through wired or wireless connections as will be appreciated by those skilled in the art. Other sensor assemblies include adjustable-length proximity sensor probe assemblies 110 and 112, which, as illustrated in the example embodiment of FIG. 1, are disposed fully within the interior of motor housing 12.

A first pair of brackets 116, 118 is provided to maintain sensor tip assembly 120 of penetrator assembly 102 and the sensor tip assembly 122 of proximity probe assembly 110 adjacent motor shaft 14 in an angularly displaced relationship to one another. In some embodiments, sensor tip assembly 120 and sensor tip assembly 122 are generally orthogonal to one another. Sensor tip assemblies 120, 122 are generally aligned along a radial axis with respect to motor shaft 14. Similarly, a second pair of brackets 126, 128 is provided to maintain sensor tip 130 of penetrator assembly 104 and sensor tip 132 of probe assembly 112 at adjacent motor shaft 14 in an orthogonal relationship to one another. Also, bracket 136 is provided to maintain sensor tip 138 adjacent interior end 16 of motor shall 14 in an orthogonal relation to sensor tip assemblies 130, 132.

In the embodiment illustrated in FIG. 1, sensor tip assemblies 120, 122, 130, 132, 138 include a coil of an eddy current (EC) sensor. As one skilled in the art will appreciate, the coil of an eddy current sensor generates a magnetic field, which in turn, generates small electric currents (called eddy currents) in a conductive target such as motor shaft 14. The eddy currents create a magnetic field that opposes the magnetic field generated by the coil, and the interaction of the magnetic fields is dependent upon a distance between the coil and the target. In other embodiments, alternate types proximity sensors or non-contact position or range sensors may be employed such as LVDT's (linear variable differential transformers), capacitive sensors, photoelectric sensors, sonically operated devices and digital or optical encoders.

Sensor tip assemblies 120, 122, 130, 132, 138 may be described as "pressure-compensated" at least since the sensor probe assemblies 100, 110, 112 include features that are operable to permit a portion of an exterior or environmental pressure to which the sensor probe assemblies 100, 110, 112 are exposed to be transmitted to interior portions of the proximity sensor tip assemblies 120, 122, 130, 132, 138 as described in greater detail below. This pressure compensation offers protection to the sensor tip assemblies 120, 122, 130, 132, 138 and the eddy current sensor coils to facilitate operation within high pressure environments.

The interaction between the magnetic fields is detectable by electronics such as those electronics contained in electronic packages 108. In this manner, sensor tips 120, 122, 130, 132 and 138 are operable to monitor a position of motor shaft 14 along two sets of axially-spaced, x-y axes and along a z-axis. In the illustrated embodiment, each pair of sensor tips associated with a particular x-y axis, e.g., sensor tips 120, 122 and sensor tips 130, 132, are operatively coupled to a common electronics package 108 and the sensor tip 138 associated with the z-axis is operatively coupled to a separate electronics package. In other embodiments, a single electronics package 108 is operatively associated with each of sensor tips 120, 122, 130, 132 and 138, and in other embodiments, each sensor tip 120, 122, 130, 132 and 138 is associated with a separate electronics package 108.

An internal motor cavity 40 is defined between motor housing 12 and motor shaft 14. In some embodiments, internal motor cavity 40 is filled with a barrier fluid such as an oil, glycol, water or a combination of different fluids. Barrier fluids provide a clean operating environment for bearing assemblies 30, 32 and provide other benefits as appreciated by those skilled in the art.

Internal motor cavity 40 is irregularly shaped, and in some locations defines a serpentine path between motor housing 12 and motor shaft 14. To properly position sensor tips 120, 122, 130, 132 and 138 adjacent motor shaft 14, integrated penetrator and proximity sensor probe assemblies 102, 104, 106 and proximity sensor probe assemblies 110 and 112 are configured to be flexible and adjustable in some embodiments. In some instances, a straight and/or substantially rigid penetrator assembly 102 can be provided where sufficient space exists between motor housing 12 and motor shaft 14. In other instances, a curved (flexible or substantially rigid) integrated penetrator and proximity sensor probe assembly 104 and/or proximity sensor probe assembly 112 is provided which curves to accommodate the position of internal motor components such as stator 24 and base 38 without interfering therewith.

Figure 2:
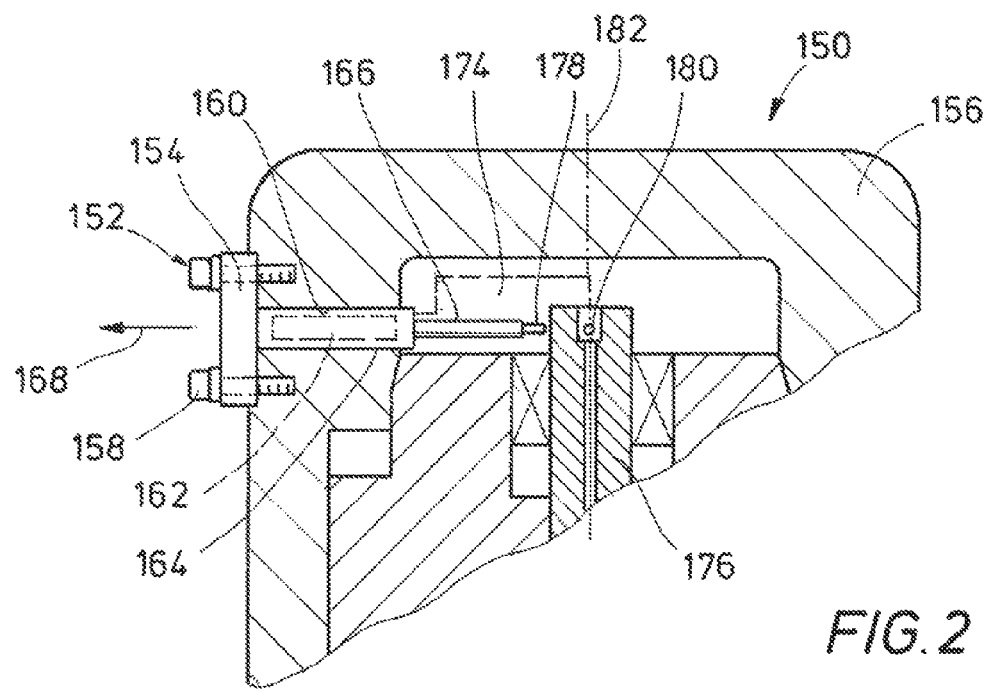
FIG. 2 is a partial environmental view of subsea pump assembly including an integrated penetrator and sensor assembly in accordance with an embodiment of the present invention.

Referring to FIG. 2, subsea pump assembly 150 is another example subsea device, which includes an integrated penetrator and proximity sensor probe assembly 152. The integrated penetrator and sensor assembly 152 includes a proximal penetrator housing 154, which is mounted directly to an exterior of pump housing 156 by fasteners 158. Proximal penetrator housing 154 extends through an opening 160 defined through a wall of pump housing 156 and forms a seal with the opening 160. Electronics package 162 is disposed within an interior of the pump housing 156. In particular, electronics package 162 is disposed within the proximal penetrator housing 154 and within the opening 160 extending through the wall of the pump housing 156. This arrangement of the electronics package 162 within the opening 160 provides protection to the electronics package 162 from damage by debris in the subsea environment and permits the integrated penetrator and proximity sensor probe assembly 152 to maintain a low profile outside the pump housing 156. Electronics package 162 is disposed within an electronics housing 164, which defines a portion of proximal penetrator housing 154. Electronics housing 164 is configured to maintain a nominal 1-atmosphere environment therein when exposed to an external pressure of about 1035 bar. In some embodiments, e.g., electronics housing 164 is configured to maintain a pressure therein of less than 2 atmospheres when exposed to both a 1-atmosphere ambient environment and a 1035 bar ambient environment.

As indicated by arrow 168, electronics package 162 is operable to communicate information related to parameters detected by the integrated penetrator and proximity sensor probe assembly 152 to equipment exterior to the integrated penetrator and proximity sensor probe assembly 152. For example, in some embodiments, electronics package 162 is operatively coupled to a data acquisition (DAQ) module (not shown) for processing and/or storage of data provided by integrated penetrator and sensor assembly 152. In some embodiments, electronics package 162 is coupled to the DAQ module through wired or wireless connections as will be appreciated by those skilled in the art.

Distal penetrator housing 166 extends from proximal penetrator housing 154 into internal pump cavity 174 defined between pump housing 156 and pump shaft 176. Proximal and distal penetrator housing 154, 166 are sufficiently rigid such that proximity sensor tip assembly 178 is substantially stationary with respect to pump housing 156 during rotation or dynamic operation of pump shaft 176. In this manner, proximity sensor tip assembly 178 is cantilevered by a wall of the pump housing 156, and is operable to sense a displacement of pump shaft 176 between a static configuration wherein pump shaft 176 is stationary with respect to pump housing 156 and a dynamic configuration wherein pump shaft 176 rotates within pump housing 156. Pump shaft 176 can be coupled to motor shaft 14 (FIG. 1) such that the pump shaft 176 is driven by motor shaft 14 as recognized by those skilled in the art. In other embodiments (see FIG. 3), portions of the distal penetrator housing 186 are flexible and/or adjustable as indicated below.

Proximity sensor tip assemblies 178, 180 are generally aligned along a radial axis with respect to pump shaft 176 and in an angularly displaced relation to one another. In some embodiments, proximity sensor tip assemblies 178 and 180 are substantially orthogonal to one another, and in other embodiments sensor tips 178 and 180 are angularly spaced by an angle in the range of about 25 degrees to about 155 degrees. Sensor tip 180 is positioned at generally the same axial position along axis 182 as sensor tip 178. In other embodiments, sensor tips 178, 180 are axially displaced from one another by a predetermined distance such that a position of motor shaft 176 along a pair of x-y axes is determinable from combined positional information provided by proximity sensor tip assemblies 178, 180. Proximity sensor tip assembly 180 is operatively coupled to electronics package 162 through proximal penetrator housing 154 of integrated penetrator and proximity sensor tip assembly 152 as indicated schematically. In other embodiments (not shown), proximity sensor tip assembly 180 is integrated into another integrated penetrator and proximity sensor tip assembly (not shown) that is independently coupled to the DAQ.

Figure 3:
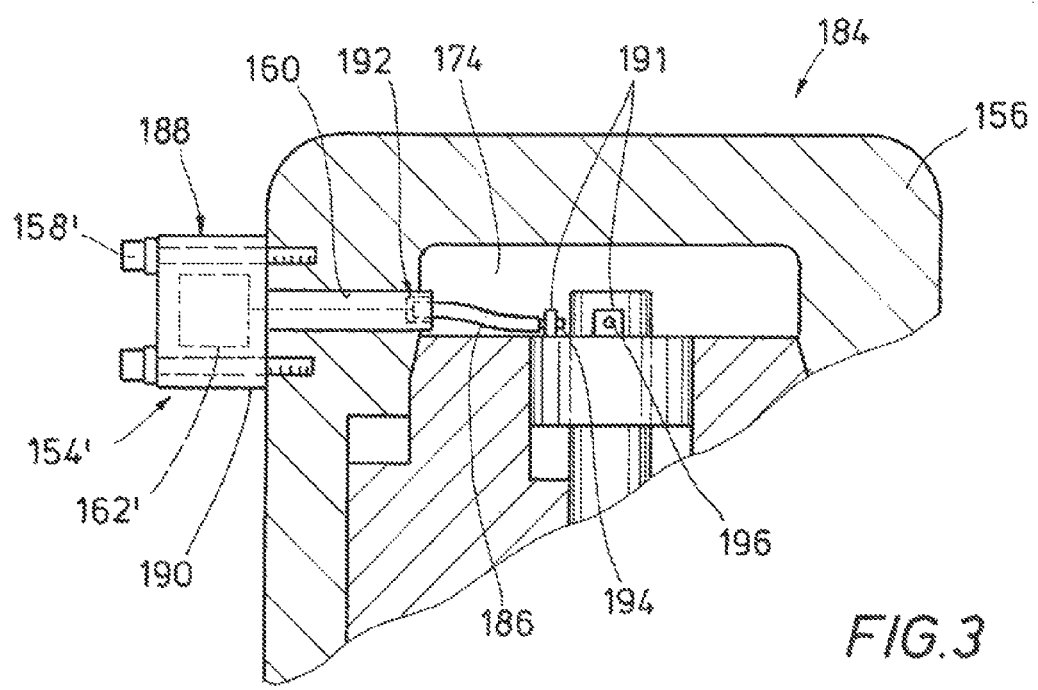
FIG. 3 is a partial environmental view of subsea pump assembly including a pair of proximity sensor assemblies in accordance with an alternate embodiment of the present invention

As shown in FIG. 3, an alternate embodiment of a subsea pump assembly 184 includes an x-axis proximity sensor probe assembly 186 that is distinct from electrical penetrator assembly 188. Electrical penetrator assembly 188 extends through opening 160 in pump housing 156 and is connected to an exterior wall of the pump housing 156 with fasteners 158'. Fasteners 158' extend through an electronics housing 190, which defines a portion of proximal penetrator housing 154'. Electronics housing 190 is configured to maintain a nominal 1-atmosphere environment therein when exposed to an external pressure of about 1035 bar. Electronics package 162' is disposed within electronics housing 190 on an exterior of pump housing 156.

Proximity sensor probe assembly 186 extends through internal pump cavity 174 along a serpentine path between pump housing 156 and mounting block 191. A connector 192 is provided to couple proximity sensor probe assembly 186 to proximal penetrator housing 154' and thereby communicatively couple proximity sensor tip assembly 194 to electronics package 162'. Mounting block 191 includes a clamp, threads or another fixation mechanism to maintain proximity sensor tip assembly 194 of proximity sensor probe assembly 186 at a fixed location with respect to pump housing 156. An end of proximity sensor probe assembly 186 opposite proximity sensor tip assembly 194 is also maintained at fixed location with respect to pump housing 156 by connector 192 or another fixation mechanism (not shown) provided on electrical penetrator assembly 188. The serpentine path taken between the opposing fixed ends of proximity sensor probe assembly 186 permits proximity sensor probe assembly 186 to accommodate alternate motor, pump or other subsea device assemblies (not shown) having a rotating shaft spaced from a device housing by a different dimension. In some embodiments, a proximity sensor tip assembly 196 or a y-axis proximity sensor probe assembly is also operatively coupled to electronics package 162' through electrical penetrator assembly 188.

Figure 4:
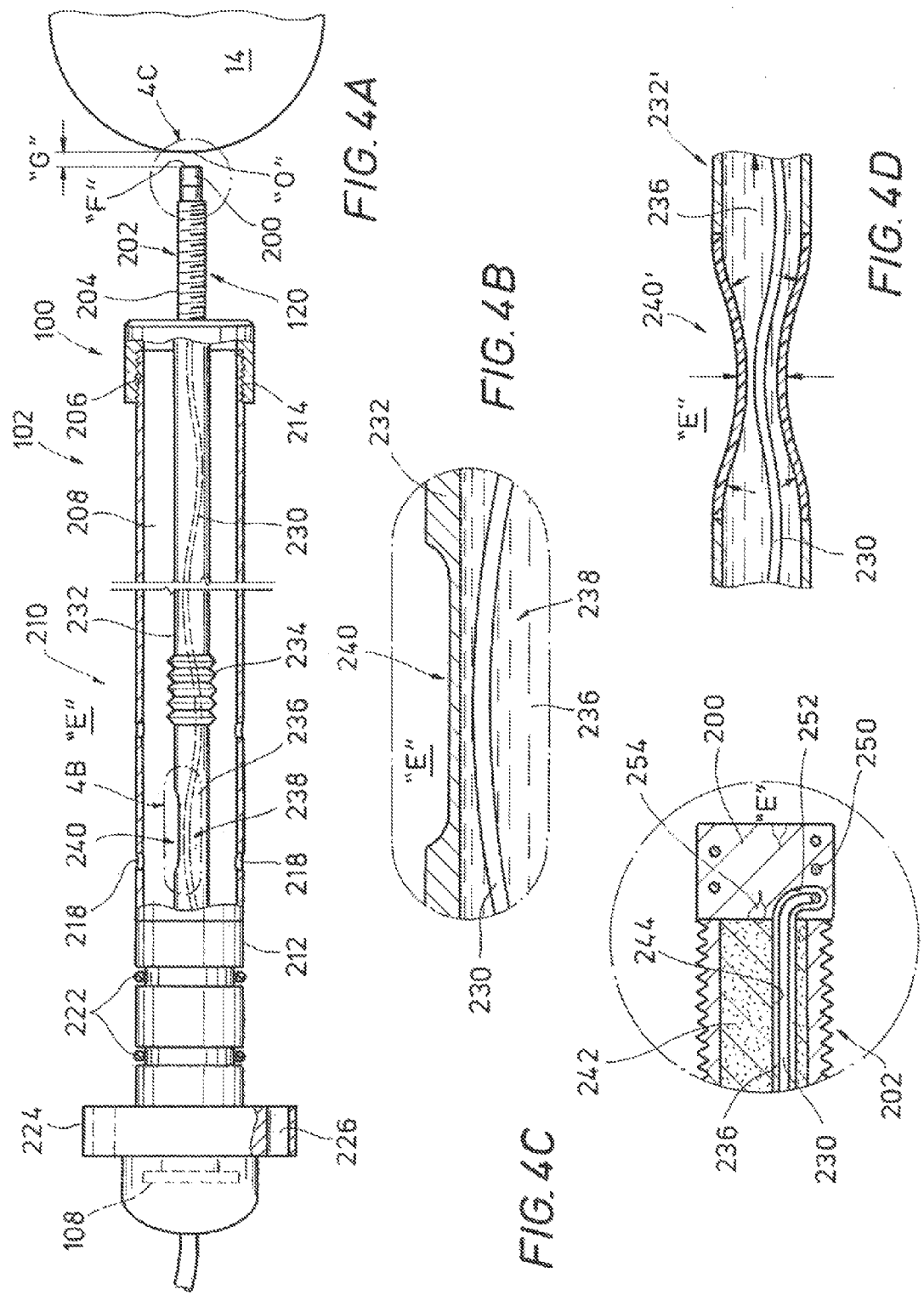
FIG. 4A is a schematic view of a subsea penetrator assembly with an adjustable-length proximity sensor probe assembly integrated therewith according to an embodiment of the present invention.
FIG. 4I is an enlarged, cross-sectional view of the area of interest identified in FIG. 4A illustrating a diaphragm or pliable membrane of the sensor probe assembly according to an embodiment of the present invention.
FIG. 4C is an enlarged cross-sectional view of the area of interest identified in FIG. 4A illustrating an interior portion of a proximity sensor tip assembly according to an embodiment of the present invention.
FIG. 4D is a cross-sectional view of an alternate pliable membrane according to an embodiment of the present invention.

Referring now to FIG. 4A, integrated penetrator and proximity sensor probe assembly 102 is arranged such that proximity sensor tip assembly 120 is proximate motor shaft 14. Proximity sensor tip assembly 120 includes proximity sensor cap 200 at distal or free end thereof. A sensing element 250 (see FIG. 4C) is disposed within proximity sensor cap 200 that is configured to produce a signal indicative of a distance between the proximity sensor cap 200 and motor shaft 14 or other target proximate the proximity sensor cap 200. In this exemplary configuration, the sensing element 250 is an eddy current coil. The proximity sensor tip assembly 120 also includes a mounting section 202 having distal threads 204 and proximal threads 206. Distal threads 204 facilitate mounting the proximity sensor tip assembly 120 to structures such as mounting blocks 190 (FIG. 3) in other embodiments. The proximal threads 206 facilitate mounting proximity sensor tip assembly 120 to distal portion 208 of penetrator housing 210. Proximal threads 206 are operable to adjust a gap "G" between proximity sensor cap 200 and motor shaft 14. Gap "G" represents a distance between a distal face "F" of the proximity sensor cap 200 and an outer surface "O" of the motor shaft 14. When motor shaft 14 is in a static state such that motor shaft 14 is stationary with respect to motor housing 12, gap "G" can be adjusted such that proximity sensor cap 200 is sufficiently close to motor shaft 14 to permit the sensing element 250 to detect motor shaft 14 and sufficiently remote from motor shaft 14 such that motor shaft 14 does not contact or damage proximity sensor cap 200 during dynamic operation of motor shaft 14 in which the motor shaft 14 may take a radially elliptical orbit (in an x-y plane) and/or take on a reciprocating motion in a longitudinal direction (along a z-axis). Once an appropriate gap "G" is achieved, a nut, clamp or other fixation mechanism (not shown) is applicable to maintain the position of proximity sensor tip assembly 120 with respect to distal portion 208 of penetrator housing 210.

Penetrator housing 210 includes distal portion 208 and proximal portion 212. Distal portion 208 structurally and mechanically couples proximal portion 212 to proximity sensor tip assembly 120. In some embodiments, distal portion 208 is a substantially tubular member including exterior threads 214 at an end thereof for interfacing with proximal threads 206 of proximity sensor tip assembly 120. In some embodiments, distal portion 208 is a generally straight and substantially rigid member. In other embodiments, distal portion 208 is curved and/or flexible to accommodate a serpentine interior motor cavity (see FIG. 1) Vents 218 are provided through distal portion 208 of penetrator housing 210 such that an environmental fluid pressure, e.g., a fluid pressure of a barrier fluid within internal motor cavity 40 (FIG. 1), that is exterior to distal portion 208 is transmissible to an interior of distal portion 208 to equalize the pressure therein. Proximal portion 212 of penetrator housing 210 includes a pair of o-rings 222 to form a seal with a bulkhead or motor housing, e.g., motor housing 12 (FIG. 1). A flange 224 includes fastener bores 226 extending therethrough and facilitates coupling the proximal portion 212 of penetrator housing 210 to the bulkhead or motor housing.

Electronics package 108 is provided at an end of proximal portion 212 of penetrator housing 210. Electronics package 108 includes a housing that is sufficiently sturdy to maintain a nominally 1-atmosphere (1.02 bar) pressure therein when integrated penetrator and proximity sensor probe assembly 102 is disposed in a high-pressure environment, e.g., submerged in a 1035 bar subsea environment. Signal transmission medium 230 operatively couples electronics package to the sensing element 250 (FIG. 4C) disposed within proximity sensor cap 200. In some embodiments, signal transmission medium 230 includes one or more electrical conductors such as a coaxial cable. In other embodiments, signal transmission medium 230 includes fiber optics, sonic waveguides or other media configured to conduct power and/or information between electronics package 108 and proximity sensor cap 200. Signal transmission medium 230 is of a sufficient length to provide slack for adjustment of gap "G" for positioning the sensor tip assembly 120. The length of transmission medium 230 permits the transmission conductor to follow a serpentine path through the sensor housing 232 along which the transmission medium 230 is substantially spaced from a wall of the sensor housing 232. In example embodiments wherein the signal transmission medium 230 is an electrical conductor, the length can be sufficiently short to prohibit contact with the wall of the sensor housing 232 and thereby facilitate electrical continuity through the signal transmission medium 230.

According to the example embodiment illustrated in FIG. 4A, the integrated penetrator and proximity sensor probe assembly 102 encapsulates the sensor probe assembly 100 (FIG. 1) therein. Sensor probe assembly 100 includes sensor housing 232, signal transmission medium 230, fluid 236 and proximity sensor tip assembly 120. According to other embodiments (not shown) sensor probe assembly 100 could be replaced by other proximity sensor probes such as the proximity sensor probes described below with reference to FIGS. 5 through 9. Sensor housing 232 extends between proximal portion 212 of penetrator housing 210 and proximity sensor tip assembly 120. Sensor housing 232 includes a reinforced flexible tubing or hose through which signal transmission medium 230 extends. Opposing ends of sensor housing 232 are fixed to proximal portion 212 and proximity sensor tip assembly 120. An extendable section of sensor housing 232 such as bellows 234 having a plurality of folds is provided to permit selectively lengthening and shortening of sensor housing 232 to thereby accommodate movement of proximity sensor tip assembly 120 with respect to penetrator housing 210 for adjustment of gap "G" for positioning the sensor tip assembly 120.

A liquid or substantially incompressible fluid 236 is disposed within a fluid reservoir 238 defined on an interior sensor housing 232. Reservoir 238 is in fluid communication with sensor tip assembly 120 as described in greater detail below. Substantially incompressible fluid is hermetically sealed within sensor housing 232 and/or proximity sensor tip assembly 120. In some embodiments, fluid 236 includes a dielectric fluid such as a gel, silicon oil, mineral oil, and monoethylene glycol. In some embodiments, a sufficient quantity of fluid 234 is provided within sensor housing 232 such that an internal pressure within sensor housing 232 is greater than 1 atmosphere when integrated penetrator and proximity sensor probe assembly 102 is disposed in a 1 atmosphere environment. For example, an internal pressure may be about 1.05 atmospheres.

A wall of sensor housing 232 includes a diaphragm or pliable membrane 240. Pliable membrane 240 is operable to flex toward fluid 236 in response to an increase in an external environmental pressure to apply at least a portion of the external pressure to fluid 236. As illustrated in FIG. 4B, pliable membrane 240 is a mechanically thinned portion of a metallic wall of sensor housing 232. In other embodiments, pliable membrane 240 includes alternate materials such as plastics or elastomers, e.g., as described with reference to FIG. 4D below.

As illustrated in FIG. 4C, mounting section 202 of proximity sensor tip assembly 120 may be filled with an epoxy 242 or other material. An interior channel 244 extends through the epoxy 242 from sensor housing 232 to proximity sensor cap 200. Substantially incompressible fluid 236 fills channel 244 such that sensor housing 232 is in fluid communication with interior portions of proximity sensor cap 200. Sensing element 250 is enclosed or disposed within proximity sensor cap 200. In the illustrated embodiment, sensing element 250 is an eddy current coil, and proximity sensor cap 200 is constructed of a plastic, ceramic or other electrically insulating material capable of withstanding temperatures and pressures encountered in subsea and wellbore environments. In other embodiments, proximity sensor cap 200 is an integral end portion of mounting section 202 that contains sensing element 250, and in other embodiments, proximity sensor cap 200 is a separate and/or removable component affixed to mounting section 202. Channel 252 extends into proximity sensor cap 200 around signal transmission medium 230 and sensing element 250, and other crevices, cracks, gaps or voids 254 are present in the interior portions of proximity sensor cap 200. Substantially incompressible fluid 236 fills channel 252 and voids 254. Proximity sensor cap 200 is constructed such that an exterior face of proximity sensor cap 200 is less pliable than pliable membrane 240 to permit at least a portion of the external pressure "E" to be applied to substantially incompressible fluid 236 via pliable member 240 to increase the internal pressure of the proximity sensor cap 200 before the external pressure "E" crushes or damages the proximity sensor cap 200 as described below.

Referring now to FIGS. 4A-4C and FIG. 1, in one example embodiment of an operational procedure, integrated penetrator assembly and sensor assembly 102 is inserted into machine or motor housing 12 and affixed thereto with fasteners extending through fastener bores 226. A resulting gap "G" is evaluated by interpreting signals provided by the sensing element 250 disposed within proximity sensor cap 200. According to an example embodiment, in the event that gap "G" is determined to be unsatisfactory, integrated penetrator and proximity sensor probe assembly 102 is withdrawn from motor housing 12, and proximal threads 206 are adjusted to appropriately move proximity sensor tip assembly 120 with respect to flange 224. In response to the adjustment of internal threads 206, bellows 234 unfolds or folds to appropriately extend or retract the extendable section of sensor housing 232. Integrated penetrator and proximity sensor probe assembly 102 is re-inserted into motor housing 12 and the resulting gap "G" is again evaluated to verify a satisfactory gap "G" has been achieved. According to other embodiments, a location of brackets 116, 126 (FIG. 1) can adjusted to achieve a satisfactory gap "G."

Subsea motor assembly 10 is then submerged into a high pressure, subsea or wellbore environment where an external pressure is as much as about 1035 bar or more. In the event that motor housing 12 leaks and internal motor cavity 40 is filled with high pressure fluid, an external pressure "E" established around integrated penetrator and proximity sensor probe assembly 102 increases. Vents 218 permit the high pressure fluid to flow into penetrator housing 210 to equalize the pressure inside the walls of the distal portion 208 and to apply the external pressure "E" to sensor housing 232. External pressure "E" is applied to pliable membrane 240, which bends or flexes inward toward substantially incompressible fluid 236. In response to the flexing of pliable membrane 240, at least a portion of the external pressure "E" is applied to the substantially incompressible fluid 236 to increase the pressure within the fluid reservoir 238 and increase the internal pressure of sensor housing 232. Since the substantially incompressible fluid 236 extends into the channel 252 and voids 254 in the proximity sensor cap 200, the increased pressure of the substantially incompressible fluid 236 on interior portions of the proximity sensor cap 200 at least partially balances the increased external environmental pressure "E" applied to exterior surfaces of proximity sensor cap 200. Thus, proximity sensor cap 200 and sensing element 250 disposed therein are operable in the increased environmental pressure "E."

Substantially incompressible fluid 236 also beneficially protects electrical connections and stabilizes the electrical parameters of an RLC circuit established by sensing element 250, signal transmission medium 230 and/or electronics in electronics package 108, thus facilitating long-term sensor reliability and accuracy.

Sensing element 250 provides a signal indicative of a distance between the proximity sensor cap 200 and motor shaft 14. Specifically, the signal can be indicative of a distance between a reference point on the proximity sensor tip assembly, such as distal face "F" of the proximity sensor cap 200, and a reference point on the motor shaft 14, such as outer surface "O" of the motor shaft 14. The signal is transmitted to electronics package 108, which in some embodiments, is interpreted to measure or determine a relative position of motor shaft 14 with respect to a preselected reference position. For example, a position of the longitudinal axis "A" of the motor shaft 14 in dynamic operation thereof can be measured relative to that of the position of the longitudinal axis "A" of the motor shaft 14 in a static state, to thereby assess a degree of unbalance of subsea motor assembly 10 operating in the subsea environment. In other examples, it not necessary to correlate dynamic parameters of the motor shaft 14 to static parameters. Frequency content and direction of vibration vectors may be assessed. This assessment facilitates identification of elliptical and/or reciprocating rotational patterns of the motor shaft 14 to assess the health of upper and lower bearing assemblies 30, 32, and also facilitates diagnosis of problems such as erosion, imbalance and cracks in the motor shall 14. This assessment thereby facilitates determining if repair or replacement of the subsea motor assembly 10 is required.

Referring to FIG. 4I), an alternate embodiment of a pliable membrane 240' is constructed of a reinforced flexible hose or tubing member. In some embodiments, the reinforced flexible tubing member can include a layer of rubber or plastic with an embedded or superimposed layer of a woven or knitted mesh of wires or other reinforcing fibers. At least a portion of the wall of the sensor housing 232' is formed by the pliable membrane 240' such that at least a portion of the external pressure "E" is applied to the substantially incompressible fluid 236 in response to pliable membrane 240' flexing inward toward the substantially incompressible fluid 236. The resulting increase in the internal pressure on fluid 236 is applied to interior portions of proximity sensor cap 200 as described above.

Figure 5:
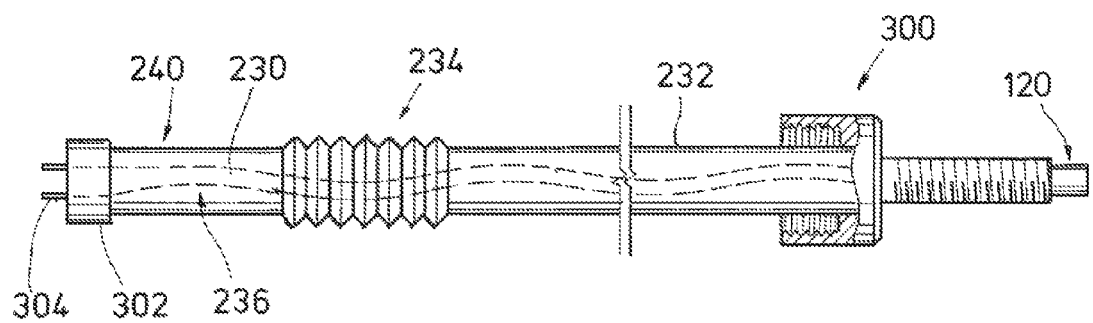
FIG. 5 is a schematic view of the adjustable-length proximity sensor probe of FIG. 4.

Referring now to FIG. 5, proximity sensor probe 300 is depicted independently of a penetrator assembly. In some embodiments, proximity sensor probe 300 could replace proximity sensor probe 100 in integrated penetrator and proximity sensor probe assembly 102. Proximity sensor probe 300 is an adjustable-length, pressure-compensated sensor probe including proximity sensor tip assembly 120 operably coupled to signal transmission medium 230, and sensor housing 232 having bellows 234, pliable membrane 240 and substantially incompressible fluid 236 sealed therein as described above. A connector or endcap 302 at a proximal end of sensor probe 300 seals substantially incompressible fluid within sensor housing 232 and proximity sensor tip assembly 120. A pair of leads 304 extends through end cap 302 and permit coupling signal transmission medium 230 to a penetrator assembly, electronics package, data acquisition module or other device as desired.

In an embodiment of an operational procedure, the proximity sensor tip assembly 120 is mounted within a device housing such as motor housing 12 (FIG. 1) or pump housing 156 (FIG. 2), e.g., with a bracket 118 (FIG. 1) or mounting block 191 (FIG. 3), to define an appropriate gap "G" (see FIG. 4A) between the proximity sensor tip assembly 120 and the rotating shaft, e.g., the motor shaft 14 (FIG. 1) or pump shaft 176 (FIG. 2). A length of the sensor housing 232 is adjusted by expanding or contracting bellows to accommodate for a range of distances between the rotating shall 14, 176 and the wall of the device housing 12, 156. An end of the sensor housing 232 opposite the proximity sensor tip assembly 120, e.g., an end adjacent endcap 302, is affixed to the wall of the device housing 12, 156. Affixing the end of the sensor housing 232 with respect to the device housing 12, 156 facilitates connection of leads 304 to an electronics package or other device as desired.

Figure 6:
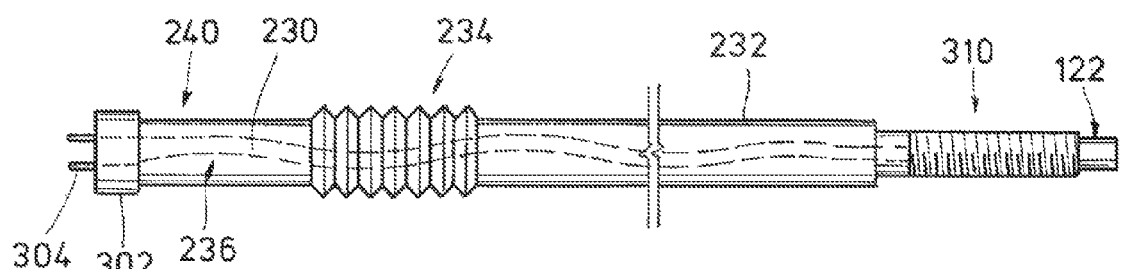
FIGS. 6 through 8 are schematic views of adjustable-length proximity sensor probes according to other example embodiments of the present invention.

As illustrated in FIG. 6, proximity sensor probe 310 is similar to proximity sensor probe 300, but differs in that proximity sensor probe 310 includes proximity sensor tip assembly 122 (see FIG. 1) rather than proximity sensor tip assembly 120. Proximity sensor tip assembly 122 facilitates coupling proximity sensor probe 310 to a bracket 118 (FIG. 1), mounting block 191 (FIG. 3) or similar mounting device. Since sensor tip assembly 122 does not necessarily couple to a penetrator housing, proximal threads 206 are not provided. Proximity sensor tip 122 is thus smaller and does not occupy so much of the internal cavity 40 (FIG. 1).

Figure 7:
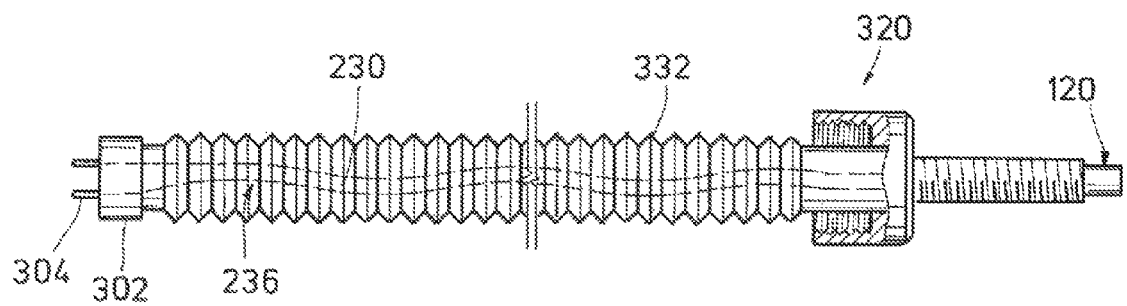
Figure 8:
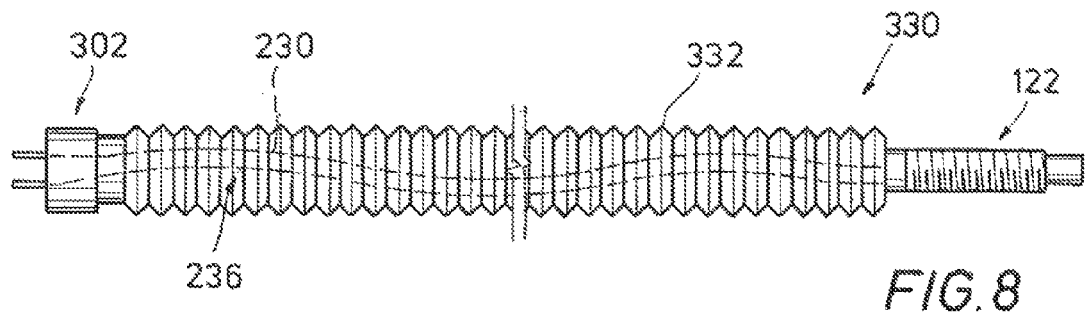

Referring now to FIGS. 7 and 8, proximity sensor probes 320 and 330 are adjustable-length, pressure-compensated sensor probes including respective proximity sensor tip assemblies 120, 122, signal transmission media 230, substantially incompressible fluid 236 and endcaps 302 as described above. Proximity sensor probes 320, 330 differ from proximity sensor probes 300, 310 in that housing 332 defines a bellows including folds extending along substantially an entire length of the housing 332. This arrangement provides additional flexibility and a length adjusting mechanism. In some embodiments, the folds in housing 332 permit housing 332 to flex inwardly toward substantially incompressible fluid 236 such that the folds are operable to apply at least a portion of an external pressure to the substantially incompressible fluid 236. In other embodiments, a separate pliable membrane (not shown) is provided on housing 332 or on endcap 302 to apply at least a portion of an external pressure to the substantially incompressible fluid 236.

Figure 9:
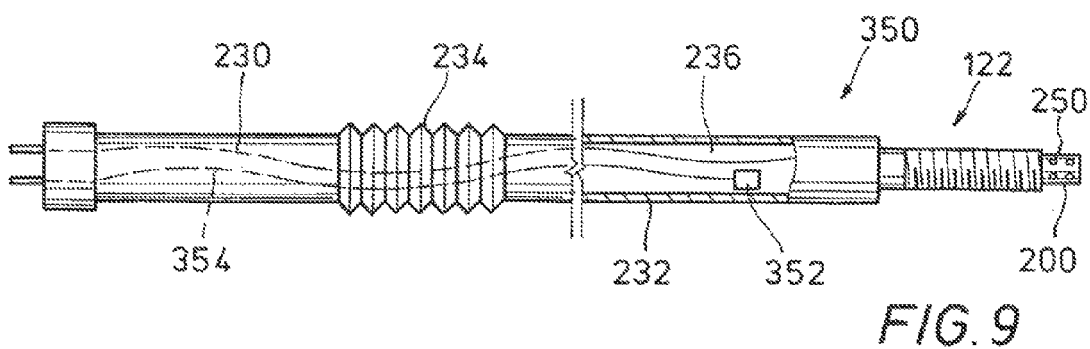
FIG. 9 is a schematic view of an adjustable-length proximity sensor probe according to an example embodiment of the present invention with an integrated sensor for monitoring a parameter of motor performance.

Referring now to FIG. 9, proximity sensor probe 350 is similar to proximity sensor probe 310 described above and includes a supplemental sensor 352 and supplemental signal transmission medium 354 disposed within substantially incompressible fluid 236. In some embodiments, supplemental sensor 352 is an acoustic or pressure sensor positioned adjacent sensing element 250 disposed within proximity sensor cap 200 of proximity sensor tip assembly 122. Sensing element 250 can provide inductive, capacitive or another type of proximity sensing for directly monitoring a position of motor shaft 14 (FIG. 1) as described above, while supplemental sensor 352 provides acoustic or pressure information to facilitate an indirect assessment of equipment health. For example, detection of pressure fluctuations having a predetermined amplitude or exhibiting predetermined regular or irregular patterns can be indications of poor motor health.

Since the internal pressure of substantially incompressible fluid 236 is a function of an environmental pressure as described above, supplemental sensor 352 is operable to indirectly sense pressures and/or acoustic waves generated by motor shaft 14. The placement of supplemental sensor 352 and supplemental signal transmission medium 354 within substantially incompressible fluid 236 protects these components from damage, and also allows supplemental sensor 352 to be positioned very near motor shaft 14 (FIG. 1). Also, a particular supplemental sensor 352 can be associated with a particular sensing element 250 such that, in some embodiments, information provided by the supplemental sensor 352 can be used to confirm a displacement detected by the associated sensing element 250. In various embodiments, the supplemental sensor 352 is a MEMS sensor, a capacitive sensor or a piezoelectric sensor. Also, in some embodiments, supplemental sensor 352 is a temperature sensor, a gyroscope, an accelerometer, a digital compass, a microphone, a hydrophone and/or other types of sensors known in the art.

In one example embodiment of an operational procedure for assembling and using a proximity sensor probe as illustrated in FIGS. 4A through 9, a proximity sensor probe is initially provided. The proximity sensor probe, as initially provided, may or may not include features that are operable to permit a portion of an environmental pressure to be transmitted to interior portions of a proximity sensor tip assembly thereof. Any voids, compressible materials and cavities where air or other compressible fluids can be contained are removed. A bellows or other extendable section is affixed to a sensor body surrounding a signal transmission medium. A pliable membrane is provided by removing material or otherwise mechanically thinning a portion of a wall the sensor body. If desired, a supplemental sensor is positioned within the body. The body is then filled with a substantially incompressible fluid, and all air or compressible fluids are forced out by the substantially incompressible fluid. The pressure of the substantially incompressible fluid can be initially increased to above one atmosphere, or alternatively can be maintained below one atmosphere. The substantially incompressible fluid can then be sealed within the body with a connector or endcap.

The proximity sensor probe can then be installed directly in machine or motor similar to proximity sensor probe 110 (FIG. 1). Alternatively, the proximity sensor probe can be connected to a penetrator housing and/or electronics package to form a penetrator assembly similar to integrated penetrator and proximity sensor probe assembly 102 (FIG. 1). The sensor probe can then be used to directly monitor a position of a rotating shaft. If a position outside a predetermined set of parameters is detected, a negative assessment of motor health may be made, and the motor may be refurbished or replaced before failure of the motor. For example, the position of the rotating shalt can be monitored to detect a synchronous vibration of the rotating shaft; a non-synchronous vibration or asynchronous vibration of the rotating shaft; and/or a sub-synchronous vibration of the rotating shaft. As appreciated by those skilled in the art, synchronous, non-synchronous and sub-synchronous vibrations can be indicators of various conditions of a rotating device such as a cracked shaft, misalignment, bearing defects, electrical faults, severe looseness, etc. The position of the rotating shaft can be monitored during various stages of dynamic operation including startup, loading and sustained operation.

Figure 10:
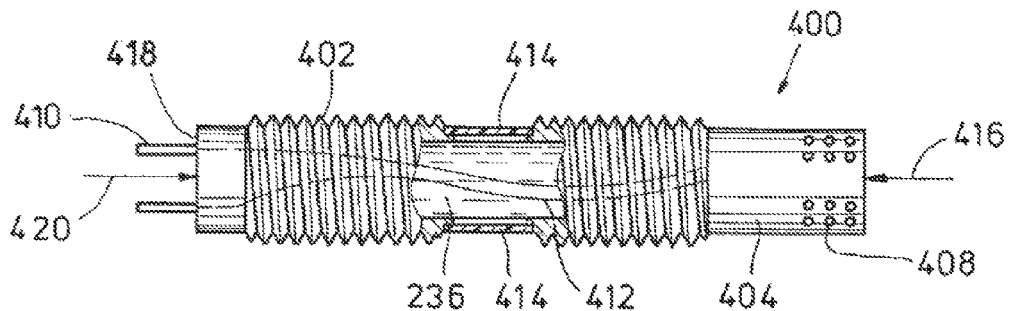
FIGS. 10 and 11 are schematic views of tips of subsea sensor probes according to other example embodiments of the present invention.
Figure 11:
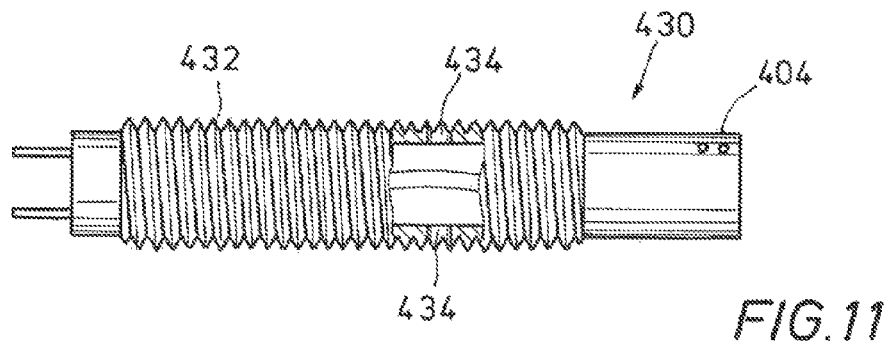

Referring now to FIG. 10, an alternate embodiment of a sensor tip assembly 400 is illustrated. Sensor tip assembly 400 includes an elongate threaded body 402, which facilitates mounting of sensor tip assembly 400 to a bracket 118 (FIG. 1) or mounting block 191 (FIG. 3). A proximity sensor cap 404, in which sensing element 408 is at least partially contained, is disposed at one end of threaded body 402. Sensing element 408 is operatively coupled to leads 410 by a signal transmission medium 412 extending through threaded body 402. Substantially incompressible fluid 236 is hermetically sealed within threaded body 402 and/or proximity sensor cap 404. Pliable membranes 414 are disposed on lateral sides of threaded body to permit at least a portion of an external environmental pressure to be applied to substantially incompressible fluid 236 within threaded body 402. In other embodiments, a pliable membrane (not shown) is disposed on a longitudinal end face of proximity sensor cap 404 as indicated by arrow 416, and/or a longitudinal end face of connector or endcap 418 as indicated by arrow 420.

As illustrated in FIG. 111, an alternate embodiment of a sensor tip assembly 430 includes an elongate threaded body 432 having vents 434 disposed therein. Vents 434 permit an environmental fluid to flow into threaded body 432 and/or proximity sensor cap 404. The environmental fluid can thus at least partially balance the internal and external pressure experienced by proximity sensor cap 404, and thereby protects sensing element 408 disposed therein.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification.

That claimed is:

1. A method of assembling and using pressure-compensated proximity sensors for monitoring the condition of a subsea rotating device, the method comprising the steps of:
    mounting a pressure-compensated proximity sensor tip assembly within a device housing of the subsea rotating device, to include disposing a sensing element within interior portions of the proximity sensor tip assembly, the sensing element configured to:
       detect a rotating shaft of the subsea rotating device and produce a signal indicative of a distance between a reference point on the proximity sensor tip assembly and a portion of the rotating shaft; and
       detect at least one of a synchronous vibration of the rotating shaft, a non-synchronous vibration of the rotating shaft, and a sub-synchronous vibration of the rotating shaft;
    mounting an end of a sensor housing connected to the proximity sensor tip assembly to a wall of the device housing, the sensor housing defining a fluid reservoir containing a substantially incompressible fluid therein that is in fluid communication with the interior portions of the proximity sensor tip assembly; and
    adjusting a length of the sensor housing to accommodate a distance between the wall of the device housing and the rotating shaft.

2. The method according to claim 1 further comprising the steps of:
    providing a proximity sensor probe, the proximity sensor probe comprising:
       a proximity sensor tip assembly having a sensing element disposed within interior portions of the proximity sensor tip assembly, the sensing element configured to detect a rotating shaft and produce a signal indicative of a distance between a reference point on the proximity sensor tip assembly and a portion of the rotating shaft;
       a sensor body connected to the proximity sensor tip assembly; and
       a signal transmission medium operatively coupled to the sensing element and extending through the sensor body;
    providing a pliable membrane to the sensor body, the pliable membrane operable to flex inward toward the fluid reservoir in response to an increase in an environmental pressure to apply a portion of the environmental pressure to the substantially incompressible fluid;
    filling the sensor body with the substantially incompressible fluid to thereby force compressible fluids out of the sensor body; and
    sealing the incompressible fluid into the sensor body.

3. The method according to claim 2, wherein the step of providing the pliable membrane to the sensor body comprises mechanically thinning a portion of the sensor body.

4. The method according to claim 2 further comprising the steps of:
    increasing the environmental pressure applied to an exterior of the sensor tip assembly and to an exterior of the sensor body; and
    transmitting a portion of the environmental pressure to the interior portions of the proximity sensor tip assembly through a pliable membrane of the sensor housing and through the substantially incompressible fluid.

5. The method according to claim 4, wherein the step of increasing the environmental pressure comprises submerging the subsea rotating device into a subsea environment.

6. The method according to claim 5 further comprising the steps of:
    dynamically operating the subsea rotating device in the subsea environment such that the rotating shaft rotates within the device housing.

7. The method according to claim 6 further comprising the steps of:
    inserting a supplemental sensor into the sensor body; and
    detecting an indirect indicator of the condition of the subsea rotating device with the supplemental sensor while dynamically operating the subsea rotating device.

8. The method according to claim 7, wherein the supplemental sensor comprises at least one of the following:
    an acoustic sensor;
    a pressure sensor;
    a temperature sensor;
    a gyroscope;
    an accelerometer;
    a digital compass;
    a microphone; and
    a hyrdrophone.

9. The method according to claim 1 further comprising the steps of:
    providing an electronics package disposed within an electronics housing and in communication with the sensing element; and
    mounting the electronics housing to an exterior of the wall of the device housing.

10. The method according to claim 1 further comprising the steps of:
    providing an electronics package disposed within an electronics housing and in communication with the sensing element; and
    mounting the electronics housing within an opening extending through the wall of the device housing.

11. A method of assembling and monitoring the condition of a subsea rotating device including a device housing and a rotating shaft disposed at least partially within the device housing, the method comprising the steps of:
    providing first and second pressure-compensated proximity sensor tip assemblies within the device housing, the first and second proximity sensor tip assemblies connected to penetrator housings, the proximity sensor tip assemblies each having a sensing element disposed within interior portions of the proximity sensor tip assembly, the sensing element configured to detect the rotating shaft and produce a signal indicative of a distance between a reference point on the proximity sensor tip assembly and a reference point on the rotating shaft;

inserting the penetrator housings through respective openings defined in the device housing to position the proximity sensor tip assemblies proximate the rotating shaft;

providing an electronics package disposed within an electronics housing defined by the penetrator housing, wherein the electronics package is communicatively coupled to the sensing elements of the first and second pressure-compensated proximity sensor tip assemblies and is operable to enable communication of information to equipment exterior to the device housing;

coupling the electronics package to a wall of the device housing;

submerging the subsea rotating device into a subsea environment such that an environmental pressure is applied to an exterior of the sensor tip assembly;

transmitting a portion of the environmental pressure to interior portions of the sensor tip assembly;

dynamically operating the subsea rotating device in the subsea environment such that the rotating shaft rotates within the device housing;

detecting a displacement of the rotating shaft between a static configuration wherein the rotating shaft is stationary with respect to device housing and a dynamic configuration wherein the rotating shaft rotates within device housing; and evaluating a resulting gap defined between the rotating shaft and the proximity sensor tip assembly.

12. The method according to claim 11 further comprising the step of providing a sensor housing connected to the proximity sensor tip assembly, the sensor housing defining a fluid reservoir containing a substantially incompressible fluid therein, and wherein the step of transmitting a portion of the environmental pressure to interior portions of the sensor tip assembly comprises applying at least a portion the environmental pressure to the substantially incompressible fluid and applying at least a portion of an internal pressure on the substantially incompressible fluid within the fluid reservoir to the interior portions of the proximity sensor tip assembly.

13. The method according to claim 12 further comprising the steps of:
mounting the pressure-compensated proximity sensor tip within the device housing to define a gap between the rotating shaft and the proximity sensor tip assembly;
mounting an end of the sensor housing opposite the proximity sensor tip assembly to a wall of the device housing; and
adjusting a length of the sensor housing to accommodate a distance between the wall of the device housing and the rotating shaft.

14. The method according to claim 12 further comprising the steps of:
providing a supplementary sensor disposed within the sensor housing and submerged within the incompressible fluid; and detecting a pressure fluctuation within the substantially incompressible fluid during dynamic operation of the rotating shaft to facilitate an indirect assessment of the condition of a subsea rotating device.

15. The method according to claim 11 further comprising the steps of:
withdrawing the penetrator housing and the proximity sensor tip assembly from the device housing;
adjusting a position of the proximity sensor tip assembly with respect to the penetrator housing; and
re-inserting the penetrator housing and the proximity sensor tip assembly through the opening defined in the device housing and evaluating an adjusted resulting gap between the rotating shaft and the proximity sensor tip assembly.

16. The method according to claim 11 further comprising the step of detecting at least one of the following: a synchronous vibration of the rotating shaft, a non-synchronous vibration of the rotating shaft, and a sub-synchronous vibration of the rotating shaft.

17. A method of assembling and using pressure-compensated proximity sensors for monitoring the condition of a subsea rotating device, the method comprising the steps of:
mounting a pressure-compensated proximity sensor tip assembly within a device housing of the subsea rotating device, to include disposing a sensing element within interior portions of the proximity sensor tip assembly, the sensing element configured to detect a rotating shaft of the subsea rotating device and produce a signal indicative of a distance between a reference point on the proximity sensor tip assembly and a portion of the rotating shaft;
mounting an end of a sensor housing connected to the proximity sensor tip assembly to a wall of the device housing, the sensor housing defining a fluid reservoir containing a substantially incompressible fluid therein that is in fluid communication with the interior portions of the proximity sensor tip assembly;
adjusting a length of the sensor housing to accommodate a distance between the wall of the device housing and the rotating shaft;
submerging the subsea rotating device into a subsea environment such that an environmental pressure is applied to an exterior of the proximity sensor tip assembly;
transmitting a portion of the environmental pressure to interior portions of the proximity sensor tip assembly;
dynamically operating the subsea rotating device in the subsea environment such that the rotating shaft rotates within the device housing; and
detecting, with the proximity sensor tip assembly, a displacement of the rotating shaft between a static configuration wherein the rotating shaft is stationary with respect to device housing and a dynamic configuration wherein the rotating shaft rotates within the device housing.

* * * * *